United States Patent [19]

Horgan et al.

[11] Patent Number: 4,507,480
[45] Date of Patent: Mar. 26, 1985

[54] SQUARAINES

[75] Inventors: Anthony M. Horgan, Pittsford, N.Y.; Peter M. Kazmaier; Richard A. Burt, both of Mississauga, Canada

[73] Assignee: Xerox Corporation, Stamford, Conn.

[21] Appl. No.: 493,113

[22] Filed: May 9, 1983

[51] Int. Cl.³ .............................. C07D 455/04
[52] U.S. Cl. ........................ 546/94; 430/59; 564/248
[58] Field of Search ............. 546/94; 564/248

[56] References Cited

U.S. PATENT DOCUMENTS 3,824,099 7/1974 Champ et al. ................ 430/58
4,150,987 4/1979 Anderson et al. ............. 430/58

Primary Examiner—Richard A. Schwartz
Attorney, Agent, or Firm—E. O. Palazzo

[57] ABSTRACT

Squaraine compositions of the following formula

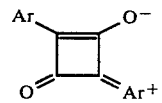

wherein Ar is selected from the moieties specified in the specification are useful for incorporation into layered photoresponsive devices.

5 Claims, 9 Drawing Figures

SQUARAINES

BACKGROUND OF THE INVENTION

This invention is generally directed to novel squaraine compositions, which can be selected for incorporation into layered photoresponsive devices. Thus, the present invention is directed to novel squaraine compositions of matter, these compositions being useful as photoconductive materials in layered photoresponsive devices, especially those devices containing diamine hole transport layers. The layered photoresponsive imaging devices involved, are the subject matter of a related co-pending application wherein it is disclosed that the sensitivity of such devices can be varied or enhanced, allowing the device to be capable of being responsive to visible light, and infrared illumination needed for laser printing. Accordingly, a layered photoresponsive device containing the novel squaraine compositions of the present invention can function so as to enhance or reduce the intrinsic properties of a charge carrier photogenerating material contained therein, in the infrared and/or visible range of the spectrum, thereby allowing this device to be sensitive to either visible light and/or infrared wavelengths.

The use of certain squaraine pigments in photoresponsive imaging devices is known, reference, for example, the disclosure contained in a copending application wherein there is described an improved photoresponsive device containing a substrate, a hole blocking layer, an optional adhesive interface layer, an inorganic photogenerating layer, a photoconductive composition capable of enhancing or reducing the intrinsic properties of the photogenerating layer, and a hole transport layer. As photoconductive compositions for this device there can be selected various squaraine pigments, including hydroxy squaraine compositions of the formula as outlined on page 13, beginning at line 21 of the copending application. Moreover, there is disclosed in U.S. Pat. No. 3,824,099, certain photosensitive hydroxy squaraine compositions. According to the disclosure of this patent the squaraine compositions are photosensitive in normal electrostatographic imaging systems.

The formation and development of electrostatic latent images on the imaging surfaces of photoconductive materials by electrostatic means is well known, one such method involving the formation of an electrostatic latent image on the surface of a photosensitive plate, referred to in the art as a photoreceptor. This photoreceptor is generally comprised of a conductive substrate containing on its surface a layer of photoconductive insulating material, and in many instances, a thin barrier layer is situated between the substrate and the photoconductive layer in order to prevent undesirable charge injection.

Numerous different xerographic photoconductive members are known including, for example, a homogeneous layer of a single material such as vitreous selenium, or a composite layered device, containing a dispersion of a photoconductive composition. An example of one type of composite xerographic photoconductive member is described for example, in U.S. Pat. No. 3,121,006, wherein there is disclosed finely divided particles of a photoconductive inorganic compound dispersed in an electrically insulating organic resin binder. In a commercial form there is coated on a paper backing a binder layer containing particles of zinc oxide uniformly dispersed in a resinous binder. The binder materials disclosed in this patent comprise a material which is incapable of transporting for any significant distance injected charge carriers generated by the photoconductive particles. Accordingly, as a result the photoconductive particles must be in a substantially contiguous particle to particle contact throughout the layer for the purpose of permitting charge dissipation required for a cyclic operation. Thus, with the uniform dispersion of photoconductive particles described a relatively high volume concentration of photoconductor material, about 50 percent by volume, is usually necessary in order to obtain sufficient photoconductor particle to particle contact for rapid discharge. This high photoconductive loading can result in destroying the physical continuity of the resinous binder, thus significantly reducing the mechanical properties thereof. Illustrative examples of specific binder materials disclosed in this patent include, for example, polycarbonate resins, polyester resins, polyamide resins, and the like.

There are also known photoreceptor materials comprised of inorganic or organic materials wherein the charge carrier generating, and charge carrier transport functions are accomplished by discrete contiguous layers. Additionally, layered photoreceptor materials are disclosed in the prior art which include an overcoating layer of an electrically insulating polymeric material. However, the art of xerography continues to advance and more stringent demands need to be met by the copying apparatus in order to increase performance standards, and to obtain higher quality images. Also, there is desired layered photoresponsive devices which are responsive to visible light, and/or infrared illumination needed for laser printing.

Recently, there has been disclosed other layered photoresponsive devices including those comprised of separate generating layers, and transport layers as described in U.S. Pat. No. 4,265,990, and overcoated photoresponsive materials containing a hole injecting layer, overcoated with a hole transport layer, followed by an overcoating of a photogenerating layer, and a top coating of an insulating organic resin, reference U.S. Pat. No. 4,251,612. Examples of photogenerating layers disclosed in these patents include trigonal selenium, and phthalocyanines, while examples of transport layers include certain diamines as mentioned herein. The disclosures of each of these patents, namely, U.S. Pat. Nos. 4,265,990 and 4,251,612 are totally incorporated herein by reference.

Many other patents are in existence describing photoresponsive devices including layered devices containing generating substances, such as U.S. Pat. No. 3,041,167, which discloses an overcoated imaging member containing a conductive substrate, a photoconductive layer, and an overcoating layer of an electrically insulating polymeric material. This member is utilized in an electrophotographic copying method by, for example, initially charging the member, with an electrostatic charge of a first polarity, and imagewise exposing to form an electrostatic latent image which can be subsequently developed to form a visible image. Prior to each succeeding imaging cycle, the imaging member can be charged with an electrostatic charge of a second polarity, which is opposite in polarity to the first polarity. Sufficient additional charges of the second polarity are applied so as to create across the member a net electrical field of the second polarity. Simultaneously, mobile charges of the first polarity are created in the photoconductive layer such as by applying an electrical potential to the conductive substrate. The imaging potential which is developed to form the visible image, is present across the photoconductive layer and the overcoating layer.

There is also disclosed in Belgium Pat. No. 763,540, an electrophotographic member having at least two electrically operative layers, the first comprising a photoconductive layer which is capable of photogenerating charge carriers, and injecting the carriers into a continuous active layer containing an organic transporting material which is substantially non-absorbing in the spectral region of intended use, but which is active in that it allows the injection of photogenerated holes from the photoconductive layer and allows these holes to be transported through the active layer. Additionally, there is disclosed in U.S. Pat. No. 3,041,116, a photoconductive material containing a transparent plastic material overcoated on a layer of vitreous selenium contained on a substrate.

Furthermore, there is disclosed in U.S. Pat. Nos. 4,232,102 and 4,233,383, photoresponsive imaging members comprised of trigonal selenium doped with sodium carbonate, sodium selenite, and trigonal selenium doped with barium carbonate and barium selenite.

While photoresponsive devices containing the above-described known squaraine materials are suitable for their intended purposes, there continues to be a need for the development of improved devices, particularly layered devices, containing novel squaraine materials. Additionally, their continues to be a need for novel squaraine materials which when selected for layered photoresponsive imaging devices allow the generation of acceptable images, and wherein such devices can be repeatedly used in a number of imaging cycles without deterioration thereof from the machine environment or surrounding conditions. Moreover, their continues to be a need for improved layered imaging members wherein the materials selected for the respective layers are substantially inert to users of such devices. Furthermore, their continues to be a need for overcoated photoresponsive devices which are sensitive to a broad range of wavelengths, and more specifically are sensitive to infrared light, and visible light, thereby allowing such devices to be used in a number of imaging and printing systems. Additionally, there continues to be a need for improved photoresponsive devices which can be prepared with a minimum number of processing steps, and wherein the layers are sufficiently adhered to one another to allow the continuous use of such devices in repetitive imaging and printing systems. Also, there continues to be a need for new squaraine compositions, which can be used as photoconductive substances in layered photoresponsive devices.

SUMMARY OF THE INVENTION

It is therefore an object of the present invention to provide novel squaraine compositions which are useful as photoconductive substances in photoresponsive imaging members.

It is yet another object of the present invention to provide novel squaraines for incorporation into improved photoresponsive devices, rendering such devices panchromatic, and thus sensitive to visible light as well as infrared light.

A further specific object of the present invention is the provision of an improved overcoated photoresponsive device containing a photoconductive layer comprised of novel squaraine photosensitive pigments, and a diamine hole transport layer.

It is yet another object of the present invention to provide novel squaraines for incorporation into an improved overcoated photoresponsive device containing a hole transport layer, and coated thereover a photoconductive layer containing the novel squaraine compositions.

In yet another object of the present invention there is provided a photoresponsive device containing a photoconductive composition comprised of novel squaraine compositions situated between a hole transport layer, and a photogenerating layer.

It is yet another object of the present invention to provide an improved layered overcoated photoresponsive device containing a novel squaraine photoconductive composition situated between a photogenerating layer, and the supporting substrate of such a device.

Another object of the present invention resides in the provision of an improved overcoated photoresponsive device containing a photogenerating composition situated between a hole transport layer and a photoconductive layer comprised of novel squaraine compositions, which device is simultaneously responsive to infrared light and visible light.

Another object of the present invention resides in the provision of an improved overcoated photoresponsive device containing a photoconductive layer comprised of novel squaraine composition described herein, situated between a hole transport layer, and a layer comprised of a photogenerating composition, which device is simultaneously responsive to infrared light and visible light.

In yet another embodiment of the present invention there are provided imaging and printing methods with the improved overcoated photoresponsive devices described herein.

These and other objects of the present invention are accomplished by the provision of photoresponsive devices containing novel squaraine compositions of matter of the following formula:

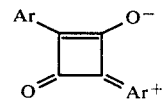

wherein Ar is selected from the moieties specified resulting in the following squaraines;

I. bis-9-(8-hydroxyjulolidinyl)squaraine

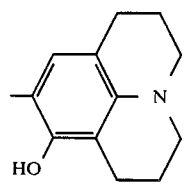

II. bis-9-(8,10-dihydroxyjulolidinyl)squaraine

-continued

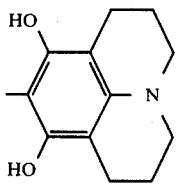

III. bis(4-dimethylamino-2-methylthiophenyl)squaraine

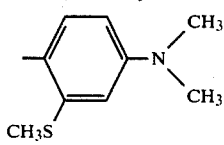

and

IV. bis(2,6-dihydroxy-4-dimethylaminophenyl)squaraine

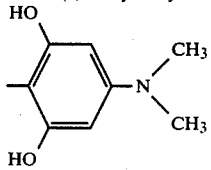

Illustrative examples of specific novel squaraine compositions included within the scope of the present invention and embraced by the above formulas, are bis-9-(8-hydroxyjulolidinyl)squaraine, bis-9-(8,10-dihydroxyjulolidinyl)squaraine, bis(4-dimethylamino-2-methylthiophenyl)squaraine, bis(2,6,-dihydroxy-4-dimethylaminophenyl)squaraine, bis(4-dimethylamino-2-mercaptophenyl)squaraine, and the like.

Preferred squaraine compositions of the present invention include bis-9-(8-hydroxyjulolidinyl)squaraine, bis(4-dimethylamino-2-methylthiophenyl)squaraine, and bis(2,6-dihydroxy-4-dimethylaminophenyl)-squaraine, primarily because of their ease of preparation, their photosensitivity response, and other electrical, chemical, and physical properties.

The novel squaraine compositions described are generally prepared by the reaction of an aromatic amine and squaric acid, in a molar ratio of from about 1.5:1 to 3:1, and preferably in a ratio of 2:1, in the presence of a mixture of an aliphatic alcohol, and an optional azeotropic cosolvent. About 200 milliliters of alcohol per 0.1 mole of squaric acid are used, however up to 1,000 milliliters of alcohol per 0.1 mole of squaric acid can be used. Also from about 40 milliliters to about 4,000 milliliters of azeotropic material is selected. The reaction is usually accomplished at a temperature of from about 50° C. to about 130° C., and preferably at a temperature of 105° C. with stirring, until the reaction is completed. Subsequently, the desired product is isolated from the reaction mixture by known techniques such as filtration. The product is then identified by analytical tools including NMR, and mass spectroscopy. Further, carbon, hydrogen, sulfur, nitrogen, oxygen elemental analysis was selected for aiding in identifying the resulting product. Illustrative examples of amine reactants include 8-hydroxyjulolidine, 8,10,dihydroxyjulolidine, N,N,-dimethyl-3-(methylthiobenzenamine), 5-dimethylaminoresorcinol, 3-dimethylaminothiophenol, and the like.

While many of the amine reactant materials are commercially available, N,N-dimethyl-3-(methylthio)benzenamine, and 8,10-dihydroxyjulolidine are not readily available nor is it believed the preparation of these amines are described in the prior art. The apparently novel intermediate amine reactant N,N-dimethyl-3-(methylthio)benzenamine was generally prepared by the alkylation of 3-aminoanisole with trimethylphosphate, while the aromatic amine 8,10-dihydroxyjulolidine was prepared from the commercially available amine 3,5-dimethoxyaniline. More specifically, the amine intermediate N,N-dimethyl-3-(methylthio)benzenamine is prepared by the alkylation of 3-aminoanisole with trimethylphosphate, the molar ratio of reactants being from about 0.2 to 1, up to about 2.0 to 1, by heating the above reactants at temperature of from about 100° C. to about 225° C. for a period of from about 0.5 hours to about 6 hours. Subsequently, the cooled reaction mixture is hydrolyzed by the addition of an aqueous base, such as sodium hydroxide or potassium hydroxide, and thereafter this mixture is heated to a temperature up from about 30° C. to about 100° C., for a period of from about 1 hour to about 5 hours. Additional sodium hydroxide is then added to the reaction mixture, which is stirred at room temperature for a period of from about 1 hour to about 20 hours. Sufficient water is then added to the reaction mixture for the purpose of preventing precipitation of the sodium or potassium phosphate being formed. The resulting product is then isolated by known techniques, such as decanting the aromatic amine layer formed, or extracting the aromatic amine into a suitable organic solvent, such as diethylether. The benzenamine product can be identified by analytical procedures, including NMR analysis, and boiling point data.

With regard to the aromatic amine 8,10-dihydroxyjulolidine, this material was obtained by dissolving from about 0.1 moles to about 10 moles, of 3,5-dimethoxyaniline in from about 50 milliliters to about 10 liters of a mixture of 1-bromo-3-chloropropane, and a solvent such as diglyme. The reaction mixture was then heated to a temperature of from about 60° C. to about 140° C. This reaction mixture was continually monitored by high performance liquid chromatography, until the reaction mixture consisted mainly of 8,10-dimethoxyjulolidine. This phase of the reaction was accomplished in a period of from about 5 hours to about 50 hours. The product 8,10-dimethyoxyjulolidine was then isolated by well-known techniques, such as distillation, after precipitation of the impurities with a nonsolvent, such as diethyl ether, an/or column chromatography. This product can then be identified by its physical properties, such as melting point, or standard characterization techniques, including NMR.

Subsequently, the resulting 8,10-dimethoxyjulolidine was converted to the squaraine precursor aromatic amine, 8,10-dihydroxyjulolidine by dissolving from about 0.1 moles to about 1 mole of the above prepared 8,10-dimethoxyjulolidine, in from about 50 milliliters to about 300 milliliters, of a chlorinated solvent such as dichloromethane. Boron tribromide, in an amount of from about 0.1 moles to about 25 moles was then added to the reaction mixture. The reaction mixture was then stirred for a period of from about 2 hours to about 24 hours, while simultaneously heating at a temperature of from 18° C. to 30° C. This mixture was then treated with water for the purpose of eliminating the boron tribromide and the resulting 8,10-dihydroxyjulolidine product was isolated by known techniques, such as solvent evaporation, and column chromatography. The product can be identified by for example melting point data, and NMR.

Illustrative examples of aliphatic alcohols selected for the preparation of the novel squaraines of the present invention include aliphatic alcohols such as 1-butanol, 1-pentanol and 1-octanol, while illustrative examples of azeotropic materials that can be used include aromatic compositions such as benzene, toluene and xylene.

In one embodiment, the improved layered photoresponsive devices involved are comprised of a supporting substrate, a hole transport layer, and a photoconductive layer containing the novel squaraines situated between the supporting substrate and the hole transport layer. In another embodiment there is envisioned a layered photoresponsive device comprised of a substrate, a photoconducing layer comprised of the novel squaraine compositions disclosed herein, and situated between the photoconducting layer and the supporting substrate, a hole transport layer. Additionally the improved photoresponsive device, which is useful in printing systems, contains a layer of the squaraine photoconductive composition situated between a photogenerating layer and a hole transport layer, or wherein the photoconductive squaraine composition layer is situated between the photogenerating layer and the supporting substrate of such a device. In the latter devices the photoconductive layer comprised of the novel squaraines composition serves to enhance or reduce the intrinsic properties of the photogenerating layer in the infrared and/or visible range of the spectrum.

In one specific illustrative embodiment, the novel squaraines are incorporated into an improved photoresponsive device comprised in the order stated of (1) a supporting substrate, (2) a hole blocking layer, (3), an optional adhesive interface layer, (4) an organic photogenerator layer, (5) a photoconducting composition layer capable of enhancing or reducing the intrinsic properties of the photogenerating layer, which composition is comprised of the novel squaraine materials described herein, and (6) a diamine hole transport layer. In one important illustrative embodiment the photoresponsive device involved can thus be comprised of a conductive supporting substrate, a hole blocking metal oxide layer in contact therewith, an adhesive layer, an inorganic photogenerating material overcoated on the adhesive layer, a photoconducting composition capable of enhancing or reducing the intrinsic properties of the photogenerating layer in the infrared and/or visible range of the spectrum, which composition is comprised of the novel squaraine compositions disclosed herein, and as a top layer, a hole transport layer comprised of certain diamines dispersed in a resinous matrix. The photoconductive layer composition when in contact with the hole transport layer is capable of allowing holes generated by the photogenerating layer to be transported. Further the photoconductive layer should not substantially trap holes generated in the photogenerating layer. Also, the photoconductive composition can function as a selective filter, allowing light of a certain wavelength to penetrate the photogenerating layer.

In another important embodiment, the squaraines of the present invention are incorporated into a photoresponsive device as described hereinbefore, with the exception that the photoconductive composition capable of enhancing or reducing the intrinsic properties of the photogenerating layer is situated between the photogenerating layer and the supporting substrate contained in the device. Accordingly, in this variation, the photoresponsive device is comprised in the order stated of (1) a substrate, (2) a hole blocking layer, (3) an optional adhesive or adhesion interface layer, (4) a photoconductive composition capable of enhancing or reducing the intrinsic properties of a photogenerating layer in the infrared and/or visible range of the spectrum, which composition is comprised of the novel squaraine materials disclosed herein, (5) an inorganic photogenerating layer, and (6) a hole transport layer.

Exposure to illumination and erasure of the layered photoresponsive devices of the present invention may be accomplished from the front side, the rear side or combinations thereof.

The improved photoresponsive devices involved can be prepared by a number of known methods, the process parameters and the order of coating of the layers being dependent on the device desired. Thus, for example, a three layered photoresponsive device can be prepared by vacuum sublimation of the photoconducting layer on a supporting substrate, and subsequently depositing by solution coating the hole transport layer. In another process variant, the layered photoresponsive device can be prepared by providing the conductive substrate containing a hole blocking layer and an optional adhesive layer, and applying thereto by solvent coating processes, laminating processes, or other methods, a photogenerating layer, a photoconductive composition comprised of the novel squaraines of the present invention, which squaraines are capable of enhancing or reducing the intrinsic properties of the photogenerating layer in the infrared and/or visible range of the spectrum, and a hole transport layer.

These improved photoresponsive devices can be incorporated into various imaging systems, such as those conventionally known as xerographic imaging processes. Additionally, the improved photoresponsive devices containing an inorganic photogenerating layer, and a photoconductive layer comprised of the novel squaraines of the present invention can function simultaneously in imaging and printing systems with visible light and/or infrared light. In this embodiment, the improved photoresponsive devices of the present invention may be negatively charged, exposed to light in a wavelength of from about 400 to about 1,000 nanometers, either sequentially or simultaneously, followed by developing the resulting image and transferring to paper. The above sequence may be repeated many times.

BRIEF DESCRIPTION OF THE DRAWINGS

For a better understanding of the present invention and further features thereof reference is made to the following detailed description of various preferred embodiments wherein.

The percent discharge is defined as $$\frac{V_{DDP}(-800 \text{ volts}) - V20 \text{ Ergs cm-2}}{V_{DDP}(-800 \text{ volts})} \times 100$$

where $V_{DDP}$ is the dark development potential, and

V 20 ergs cm$^{-2}$ is the surface potential on the photoreceptor after exposure to 20 ergs cm$^{-2}$ of light in the wavelength range 400 to 1,000 nonometers.

As an example, for a $V_{DDP}$ of $-800$ volts and a surface potential of 400 volts, after 20 ergs cm$^{-2}$ exposure at, for example 800 mm, the percent discharge would be a desirable 50 percent. An optimum desirable discharge is 100.

DESCRIPTION OF THE PREFERRED EMBODIMENTS

The preferred embodiments will now be illustrated with reference to specific photoresponsive devices containing novel squaraine compositions, it being noted that the compositions are the subject matter of a copending application.

Figure 1:
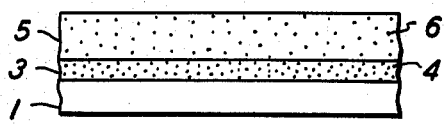
FIG. 1 is a partially schematic cross-sectional view of a photoresponsive device containing the novel squaraines of the present invention.

Illustrated in FIG. 1 is a photoresponsive device comprised of a substrate 1, a photoconductive layer 3, comprised of the novel squaraine compositions disclosed, particularly bis-9-(8-hydroxyljulolidinyl)-squaraine, optionally dispersed in a resinous binder composition 4, and a charge carrier hole transport layer 5, dispersed in an inactive resinous binder composition 6.

Figure 2:
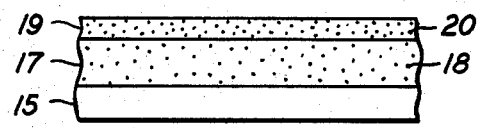
FIG. 2 is a partially schematic cross-sectional view of a photoresponsive device containing the novel squaraines of the present invention.

Illustrated in FIG. 2 is essentially the same device as illustrated in FIG. 1, with the exception that the hole transport layer is situated between the supporting substrate and the photoconductive layer. More specifically with reference to this Figure, there is illustrated a photoresponsive device comprised of a supporting substrate 15, a hole transport layer 17, comprised of a hole transport composition, dispersed in an inert resinous binder composition 18, and a photoconductive layer 19, comprised of the novel squaraine compositions of the present invention, optionally dispersed in a resinous binder composition 20.

Figure 3:
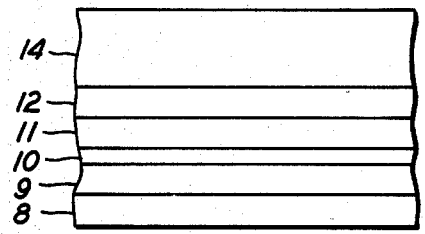
FIGS. 3 and 4 are partially schematic cross-sectional views of photoresponsive devices containing the novel squaraines embraced by the present invention.

Illustrated in FIG. 3 is an improved photoresponsive device comprised of a substrate 8, a hole blocking metal oxide layer 9, an optional adhesive layer 10, a charge carrier inorganic photogenerating layer 11, an organic photoconductive composition layer 12 comprised of the novel squaraine compositions, and capable of enhancing or reducing the intrinsic properties of the photogenerating layer 11 in the infra-red and/or visible range of the spectrum, and a charge carrier, or hole transport layer 14.

Although not specifically illustrated with reference to FIG. 3, nor with references to FIGS. 4–8, the inorganic photogenerating layer, the organic photoconductive layer, and the charge carrier hole transport layer, are comprised of the respective compositions generally dispersed in resinous binder compositions. Thus, for example, the inorganic photogenerating layer, is comprised of an inorganic photogenerating composition as illustrated herein, dispersed in an inactive resinous binder.

Figure 4:
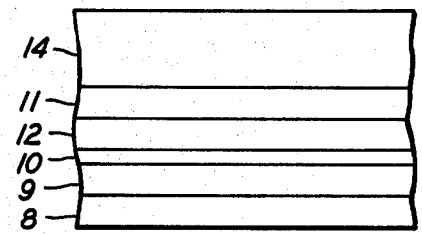

Illustrated in FIG. 4 is essentially the same device as illustrated in FIG. 3 with the exception that the photoconductive layer 12 is situated between the inorganic photogenerating layer 11 and the substrate 8, and more specifically, the photoconductive layer 12 in this embodiment is specifically situated between the optional adhesive layer 10 and the inorganic photogenerating layer 11.

Figure 5:
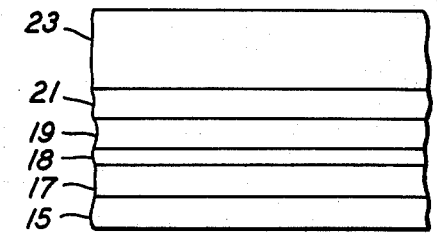
FIG. 5 is a partially schematic cross-sectional view of a photoresponsive device containing a specific novel squaraine of the present invention.

Illustrated in FIG. 5 is a preferred photoresponsive device wherein the substrate 15 is comprised of Mylar in a thickness of 3 mils. containing a layer of 20 percent transmissive aluminum in a thickness of about 100 Angstroms, a metal oxide layer 17 comprised of aluminum oxide in a thickness of about 20 Angstroms, a polyester adhesive layer 18, which polyester is commercially available from E. I. duPont as 49,000 polyester, this layer being in a thickness of 0.05 microns, an inorganic photogenerating layer 19, of a thickness of about 2.0 microns, and comprised of 10 volume percent of $Na_2SeO_3$ and $Na_2CO_3$ doped trigonal selenium, in a polyvinylcarbazole binder, 90 volume percent, a photoconductive layer 21, in a thickness of about 0.5 microns, and comprised of 30 volume percent of bis-9-(8-hydroxyjulolidinyl)squaraine, dispersed in the resinous binder Formvar, commercially available from Monsanto Chemical Company 70 volume percent and a hole transport layer 23, in a thickness of about 25 microns, comprised of 50 weight percent of N,N'-diphenyl-N,N'-bis(3-methylphenyl)-[1,1'-biphenyl]-4,4'-diamine, dispersed in a polycarbonate resinous binder.

Figure 6:
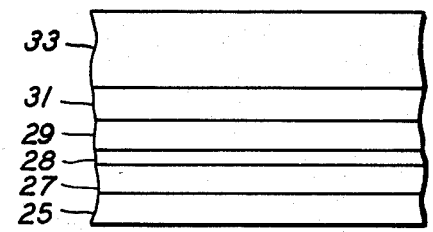
FIG. 6 illustrates a further preferred embodiment of a photoresponsive device containing a specific novel squaraine of the present invention.

Illustrated in FIG. 6 is another preferred photoresponsive device wherein layers 25, 27, 28, 29, and 33 are identical to layers 15, 17, 18, 19, and 23 as described herein with reference to FIG. 5. In FIG. 6 the photoconductive layer 31 rather than being bis-9-(8-hydroxyjulolidinyl)squaraine, is comprised of about 30 volume percent bis(4-dimethylamino-2-methylthiophenyl)-squaraine dispersed in a resinous binder material, 70 volume percent, commercially available as Formvar ® from Monsanto Chemical Company.

Figure 7:
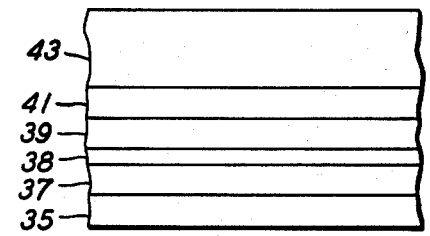
FIG. 7 illustrates another preferred embodiment of the photoresponsive device containing a specific novel squaraine of the present invention.

Illustrated in FIG. 7 is a further embodiment of a photoresponsive device wherein the substrate 35 is comprised of Mylar in a thickness of 3 mils, containing about a 100 Angstrom layer of 20 percent transmissive aluminum, the metal oxide hole blocking layer 37 is aluminum oxide in a thickness of about 20 Angstroms, the optional adhesive layer 38 is a polyester material commercially available from from E. I. duPont as 49,000 polyester, this layer being in a thickness of 0.05 microns, the photogenerating layer 39 is comprised of 33 volume percent of trigonal selenium dispersed in a phenoxy resinous binder, commercially available as the poly(hydroxyether) Bakelite from Allied Chemical Corporation, this layer having a thickness of 0.4 microns, a photoconductive layer 41, comprised of 30 percent by volume of bis-9-(8-hydroxyjulolidinyl)-squaraine dispersed in a resinous binder commercially available as Formvar ® from Monsanto Chemical Company, 70 percent by volume, which layer has a thickness of about 0.5 microns and a hole transport layer 43 in a thickness of about 25 microns, comprised of 50 percent by weight of N,N'-diphenyl-N,N'-bis(3-methylphenyl)-[1,1'-biphenyl]-4,4'-diamine, dispersed in a polycarbonate resinous binder, 50 percent by weight.

Figure 8:
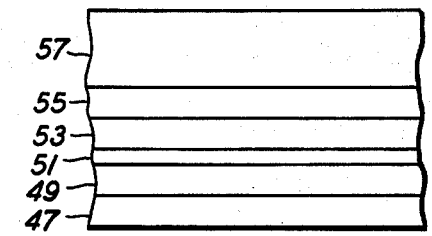
FIG. 8 illustrates another preferred embodiment of the photoresponsive device containing a specific novel squaraine of the present invention.

Illustrated in FIG. 8 is a further preferred photoresponsive device wherein the layers 47, 49, 51, 53, and 57 are identical to the layers 35, 37, 38, 39 and 43, with reference to FIG. 7. In FIG. 8, the photoconductive layer 55 is comprised of 30 volume percent of bis(4-dimethylamino-2-methylthiophenyl)squaraine dispersed in a resinous binder Formvar ®, 70 volume percent.

The substrate layers may be opaque or substantially transparent, and may comprise any suitable material having the requisite mechanical properties. Thus the substrate may comprise a layer of insulating material such as an inorganic or organic polymeric material, such as Mylar, a commercially available polymer, a layer of an organic or inorganic material having a semiconductive surface layer such as indium tin oxide, or aluminum arranged thereon, or a conductive material such as, for example, aluminum, chromium, nickel, brass or the like. The substrate may be flexible or rigid and many have a number of many different configurations, such as, for example, a plate, a cylindrical drum, a scroll, an endless flexible belt and the like. Preferably, the substrate is in the form of an endless flexible belt. In some situations, it may be desirable to coat on the back of the substrate, particularly when the substrate is an organic polymeric material, an anti-curl layer, such as for example, polycarbonate materials commercially available as Makrolon.

The thickness of the substrate layer depends on many factors, including economical considerations, thus this layer may be of substantial thickness, for example, over 100 mils, or of minimum thickness, providing there are no adverse effects on the system. In one preferred embodiment the thickness of this layer ranges from about 3 mils to about 10 mils.

The hole blocking metal oxide layers can be comprised of various suitable known materials including aluminum oxide, and the like. The preferred metal oxide layer is aluminum oxide. The primary purpose of this layer is to provide hole blocking, that is to prevent hole injection from the substrate during and after charging. Typically, this layer is of a thickness of less than 50 Angstroms.

The adhesive layers are typically comprised of a polymeric material, including polyesters, polyvinyl butyral, polyvinyl pyrrolidone and the like. Typically, this layer is of a thickness of less than about 0.3 microns.

The inorganic photogenerating layer can be comprised of known photoconductive charge carrier generating materials sensitive to visible light, such as amorphous selenium, amorphous selenium alloys, halogen doped amorphous selenium, halogen doped amorphous selenium alloys, trigonal selenium, mixtures of Groups IA and IIA elements, selenite and carbonates with trigonal selenium, reference U.S. Pat. Nos. 4,232,102 and 4,233,283, cadmium sulphide, cadmiun selenide, cadmium telluride, cadmium sulfur selenide, cadmiun sulfur telluride, cadmium seleno telluride, copper, and chlorine doped cadmium sulphide, cadmium selenide and cadmium sulphur selenide and the like. Alloys of selenium included within the scope of the present invention include selenium tellurium alloys, selenium arsenic alloys, selenium tellurium arsenic alloys, and preferably such alloys containing a halogen material such as chlorine in an amount of from about 50 to about 200 parts per million.

This layer typically has a thickness of from about 0.05 microns to about 10 microns or more, and preferably from about 0.4 microns to about 3 microns, however, the thickness of this layer is primarily dependent on the photoconductive volume loading, which may vary from 5 to 100 volume percent. Generally, it is desirable to provide this layer in a thickness which is sufficient to absorb about 90 percent or more of the incident radiation which is directed upon it in the imagewise or printing exposure step. The maximum thickness of this layer is dependent primarily upon factors such as mechanical considerations, for example whether a flexible photoresponsive device is desired.

A very important layer of the photoresponsive device of the present invention with respect to FIGS. 3–8 is the photoconductive layer which is comprised of the novel squaraine compositions disclosed herein. These compositions are generally electronically compatible with the charge carrier transport layer, in order that photoexcited charge carriers can be injected into the transport layer, and further in order that charge carriers can travel in both directions across the interface between the photoconductive layer and the charge transport layer.

Generally, the thickness of the photoconductive layer depends on a number of factors including the thickness of the other layers, and the percent mixture of photoconductive material contained in this layer. Accordingly, this layer can range in thickness of from about 0.05 microns to about 10 microns when the photoconductive squaraine composition is present in an amount of from about 5 percent to about 100 percent by volume, and preferably this layer ranges in thickness of from about 0.25 microns to about 1 micron, when the photoconductive squaraine composition is present in this layer in an amount of 30 percent by volume. The maximum thickness of this layer is dependent primarily upon factors such as mechanical considerations, for example whether a flexible photoresponsive device is desired.

The inorganic photogenerating materials or the photoconductive materials can comprise 100 percent of the respective layers, or these materials can be dispersed in various suitable inorganic or resinous polymer binder materials, in amounts of from about 5 percent by volume to about 95 percent by volume, and preferably in amounts of from about 25 percent by volume to about 75 percent by volume. Illustrative examples of polymeric binder resinous materials that can be selected include those as disclosed, for example, in U.S. Pat. No. 3,121,006, the disclosure of which is totally incorporated herein by reference, polyesters, polyvinyl butyral, Formvar ®, polycarbonate resins, polyvinyl carbazole, epoxy resins, phenoxy resins, especially the commercially available poly(hydroxyether) resins, and the like.

In one embodiment of the present invention, the charge carrier transport material, such as the diamine described hereinafter, may be incorporated into the photogenerating layer, or the photoconductive layer in amounts, for example, ranging from about zero volume percent to 60 volume percent.

The charge carrier transport layers, such as layer 14, can be comprised of a number of suitable materials which are capable of transporting holes, this layer generally having a thickness in the range of from about 5 microns to about 50 microns, and preferably from about 20 microns to about 40 microns. In a preferred embodiment, this transport layer comprises molecules of the formula:

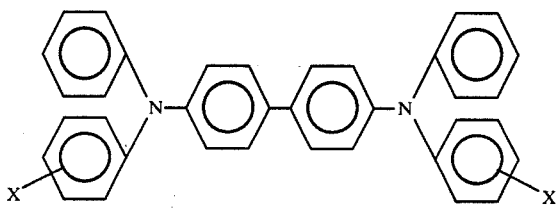

dispersed in a highly insulating and transparent organic resinous binder wherein X is selected from the group consisting of (ortho) $CH_3$, (meta) $CH_3$, (para) $CH_3$, (ortho) Cl, (meta) Cl, (para) Cl. The highly insulating resin, which has a resistivity of at least $10^{12}$ ohm-cm to prevent undue dark decay, is a material which is not necessarily capable of supporting the injection of holes from the photogenerating layer, and is not capable of allowing the transport of these holes through the material. However, the resin becomes electrically active when it contains from about 10 to 75 weight percent of the substituted N,N,N',N'-tetraphenyl[1,1-biphenyl]4-4'-diamines corresponding to the foregoing formula.

Compounds corresponding to the above formula include, for example, N,N'-diphenyl-N,N'-bis(alkylphenyl)-[1,1-biphenyl]-4,4'-diamine wherein the alkyl is selected from the group consisting of methyl such as 2-methyl, 3-methyl and 4-methyl, ethyl, propyl, butyl, hexyl and the like. In the case of chloro substitution, the compound is named N,N'-diphenyl-N,N'-bis(halo phenyl)-[1,1'-biphenyl]-4,4'-diamine wherein the halo atom is 2-chloro, 3-chloro or 4-chloro.

Other electrically active small molecules which can be dispersed in the electrically inactive resin to form a layer which will transport holes include, bis(4-diethylamine-2-methylphenyl)phenylmethane; 4',4''-bis(diethylamino)-2'2''-dimethyltriphenylmethane; bis-4(diethylaminophenyl)phenylmethane; and 4,4'-bis(diethylamino)-2,2'-dimethyltriphenylmethane.

Providing the objectives of the present invention are achieved, other charge carrier transport molecules can be selected for layer 14.

Examples of the highly insulating and transparent resinous material or inactive binder resinous material, for the transport layers include materials such as those described in U.S. Pat. No. 3,121,006 the disclosure of which is totally incorporated herein by reference. Specific examples of organic resinous materials include polycarbonates, acrylate polymers, vinyl polymers, cellulose polymers, polyesters, polysiloxanes, polyamides, polyurethanes and epoxies as well as block, random or alternating copolymers thereof. Preferred electrically inactive binder materials are polycarbonate resins having a molecular weight (Mw) of from about 20,000 to about 100,000 with a molecular weight in the range of from about 50,000 to about 100,000 being particularly preferred. Generally, the resinous binder contains from about 10 to about 75 percent by weight of the active material corresponding to the foregoing formula, and preferably from about 35 percent to about 50 percent of this material.

With further reference to the three layered devices illustrated in FIGS. 1 and 2, the supporting substrate, the hole transport layer, the photoconductive layer, and the resinous binder compositions, as well as the thicknesses thereof are as described herein. More specifically, for example, the supporting substrate layers 1 and 15 may be opaque or substantially transparent and may comprise a suitable material having the requisite mechanical properties. This substrate may comprise a layer of insulating material such as an inorganic or organic polymeric material, a layer of an organic or inorganic material having a conductive surface layer thereon, or a conductive material such as, for example, aluminum, chromium, nickel, indium, tin oxide, brass or the like. Also there can be coated on the substrate as optional layers known hole blocking layers, such as aluminum oxide and an adhesive material, such as a polyester resin, commercially available for example from Goodyear Chemical Company. The substrate may be flexible or rigid and may have any of many different configurations, such as for example, a plate, a cylindrical drum, a scroll, an endless flexible belt and the like. Preferably, this substrate is in the form of an endless flexible belt. When in the configuration of a belt, in some instances it may be desirable to apply a coating of an adhesive layer to the selected substrate, of the device of FIG. 1, for example, subsequent to the application of a hole blocking layer, such as aluminum oxide.

With further regard to FIGS. 1 and 2, the photoconductive layers 3 and 19 respectively, are comprised of the novel squaraine compositions of the present invention, especially bis-9-(8-hydroxyjulolidinyl)squaraine, optionally dispersed in a resinous binder composition, 4 and 20. These squaraines are electronically compatible with the charge transport layer, thus allowing the photoexcited charge carriers to be injected into the transport layer, and allow charge carriers to travel in both directions across the interface between the charge transport layer and the photogenerating layer.

The photoconductive squaraine pigments of the present invention are generally dispersed in a resinous binder materials 4 or 20, such as various suitable inorganic or organic binder compositions, in amounts of from about 5 percent by volume to 95 percent by volume, and preferably in amounts of from about 25 percent by volume to about 75 percent by volume. Illustrative examples of polymeric resinous binder materials that can be selected include those as disclosed, for example, in U.S. Pat. No. 3,121,006, the disclosure of which is totally incorporated herein by reference, polyesters, polyvinylbutyral, Formvar ®, polycarbonate resins, especially those commercially available as Makrolon ®, polyvinyl carbazoles, epoxy resins, phenoxy resins, commercially available as poly(hydroxyether) resins, and the like.

The hole transport layers, 5, and 17, are as illustrated herein with reference to FIGS. 3 to 8.

Also included within the scope of the present invention are methods of imaging with the photoresponsive devices illustrated herein. These methods of imaging generally involve the formation of an electrostatic latent image on the imaging member, followed by developing the image with a developer composition, subsequently transferring the image to a suitable substrate and permanently affixing the image thereto. In those environments wherein the device is to be used in a printing mode, the imaging method involves the same steps with the exception that the exposure step is accomplished with a laser device, or an image bar rather than a broad spectrum white light source. In the latter embodiment a photoresponsive device is selected that is sensitive to infrared radiation.

The following novel squaraine is also disclosed:

bis(4-dimethylamino-2 mercaptophenyl)squaraine

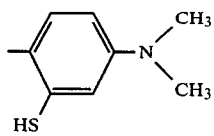

The invention will now be described in detail with reference to specific preferred embodiments thereof, it being understood that these examples are intended to be illustrative only. The invention is not intended to be limited to the materials, conditions, or process parameters recited herein, it being noted that all parts and percentages are by weight unless otherwise indicated.

EXAMPLE I

A 200 milliliter three-necked flask equipped with a Dean-Stark trap and reflux condensor was charged with squaric acid, 1.14 grams, 0.01 mol, oxygen-free n-butanol 50 milliliters and toluene 50 milliliters. The reaction mixture was heated to 95° Centigrade, and heating was continued until the squaric acid began to dissolve. When dissolution was two-thirds complete, about 15 minutes, 8-hydroxyjulolidine, 3.79 grams, 0.02 mol was added in one portion in 40 milliliters of toluene. Heating was continued to 105° C. until the reaction was complete, about 2-3 hours. On addition of the 8-hydroxyjulolidine, the colorless reaction mixture changed to a deep green. In 20 minutes when 0.1 milliliters of water had collected in the Dean-Stark trap, crystals began collecting at the bottom of the flask. After 2 hours, about 0.3 milliliters of water had collected in the Dean-Stark trap at which time the reaction was stopped by cooling to 4° C. The resulting crystals were collected on a fritted glass filter funnel and washed three times with ethyl acetate. The metallic green crystals which had a decomposition point of 255° C., were identified as bis-9-(8-hydroxyjulolidinyl)squaraine 4.33 grams, 95% yield, by infrared analysis and chemical analysis.

By decomposition at 255° C. is meant that the crystals discolored from green to black when achieving this temperature. Additionally, infrared analysis of the squaraine obtained indicated an absorption band at 1625 $cm^{-1}$, as a KBr pellet.

The visible absorption band in chloroform for the squaraine product obtained was 668 nanometers with a log of the extinction coefficient of 5.48.

| Chemical Analysis for $C_{28}H_{24}N_2O_4$ | | |
| --- | --- | --- |
| Element | Theoretical | Found |
| C | 73.66% | 72.76% |
| H | 6.18 | 6.23 |
| N | 6.14 | 6.04 |

EXAMPLE II

A 500 millilter three-necked flask equipped with a Dean-Stark trap and reflux condenser was charged with squaric acid, 3.52 grams 0.03 mol, n-butanol, 150 milliliter and toluene, 120 milliliter. The reaction mixture was then heated to 81° C. and the squaric acid began to dissolve. When dissolution was nearly complete, about 30 minutes, 8-hydroxyjulolidine, 11.5 grams, 0.06 mol in toluene, 30 milliliters was added in one portion, causing the reaction mixture to change from a clear color to deep green. Heating was continued at 105° C. until the reaction was complete, about 2 hours. After 1.2 milliliters of water had collected in the Dean-Stark trap. The product was collected on a fritted glass filter funnel and washed with ethyl acetate with agitation until the washings were pale green in color. The metallic green bis-9-(8-hydroxyjulolidinyl)squaraine was air-dried to a constant weight 13.2 grams, 96% yield. The product was then recrystallized by heating 3.0 grams of bis-9-(8-hydroxyjulolidinyl)squaraine in chloroform 1650 milliliters for 30 minutes to effect dissolution, and then slowly reducing the chloroform volume to 400 milliliters at room temperature over 3 days. Recovery 2.58 grams, 86% yield.

The metallic green crystals which had a decomposition point of 255° C. were identified as bis-9-(8-hydroxyjulolidinyl)squaraine, by infrared analysis and chemical analysis resulting in substantially identical data as reported in Example I.

EXAMPLE III

A 500 milliliter three-necked round-bottomed flask, equipped with a Dean Stark trap, reflux condenser and a nitrogen inlet was charged with squaric acid 4.46 grams, 0.039 mole, oxygen-free n-butanol, 150 milliliters and toluene, 200 milliliters. The reaction mixture was heated to reflux, and approximately 80% of the squaric acid dissolved. After refluxing of the reaction mixture had started, 5-dimethylamino-resorcinol, 12 grams, 0.078 mol was added in one portion, in 80 milliliters of toluene and the reaction mixture changed from a clear color to green. Heating was continued at 105° C. until the reaction was complete, about 2 hours, however, crystals began to form within one hour. On completion, about 0.4 milliliters of water had collected in the Dean Stark trap. The reaction mixture was then stirred at 21 degrees centigrade under nitrogen overnight.

The fine blue crystals, which were collected on a fritted glass filter and washed thoroughly with ethyl acetate, had a decomposition point of 348° C., and were identified as bis-(2,6-dihydroxy-4-dimethylaminophenyl)squaraine, 8.31 grams, a 66 percent yield, by infrared analysis and chemical analysis. This material had an infrared absorption band as a KBr pellet at 1630 $cm^{-1}$.

Additionally, mass spectroscopic analysis indicated a molecular ion of 384.

The visible absorption band in chloroform was 639 nanometers and 5.43 nanometers, respectively, with a log of the extinction coefficient being 5.429 at 639 nanometers and 4.41 at 594 nanometers.

| Chemical Analysis for $C_{20}H_{20}N_2O_6$ | | |
| --- | --- | --- |
| Element | Theoretical | Found |
| C | 62.49% | 62.80% |
| H | 5.25 | 5.55 |
| N | 7.29 | 7.28 |

EXAMPLE IV

A 3-necked, 300 milliliter round bottomed flask equipped with a thermometer, magnetic stirbar, and a 10 milliliter Dean Stark trap, topped with a condenser and nitrogen inlet was charged with squaric acid 1.72 grams, 15.1 mol, toluene, 75 milliliters, and n-butanol 75 milliliter. The mixture was stirred rapidly and heated to 90° C. over 15 minutes at which time the squaric acid started to dissolve. When dissolution was complete, N,N-dimethyl-3-(methylthio)benzenamine, 5.05 grams, 30.2 millimoles was added in one portion. The color slowly changed from clear to green indicating the formation of a squaraine composition. The reaction mixture was rapidly heated to reflux and reflux was maintained until the appearance of a brown tint.

Upon cooling to room temperature, the product, bis(4-dimethylamino-2-methylthiophenyl)squaraine was isolated as green crystals, 130 milligrams, 2.1% by filtration.

This product which had a melting point of 232° C. was identified by infrared analysis and chemical analysis. Infrared analysis as a KBr pellet showed an absorption band at 1585 cm$^{-1}$.

| Chemical Analysis for $C_{22}H_{24}N_2O_2S_2$ | | |
| --- | --- | --- |
| Element | Theoretical | Found |
| C | 64.05% | 64.15% |
| H | 5.86 | 5.91 |
| N | 6.79 | 6.87 |
| S | 15.54 | 15.52 |

EXAMPLE V

To a 500 milliliter, 3-necked round bottomed flask equipped with a Dean Stark trap, condenser, magnetic stirbar and nitrogen inlet was added squaric acid 5.48 grams, 48 mol, n-butanol, 150 milliliters and toluene, 150 milliliters. The reaction mixture was heated rapidly to reflux. 105° C. and most of the squaric acid dissolved. In one portion, N,N,-dimethyl-3-(methylthio)benzenamine, 16.1 grams, 96 millimoles in toluene, 50 milliliters was added and the refluxing continued. After 20 minutes, the solution had taken on a pale green tinge. After 3 hours crystal formation had started. Refluxing was continued for an additional hour. The product bis(4-dimethylamino-2-methylthiophenyl)squaraine was isolated by filtration. The lustrous green crystals were washed with ethyl acetate and dried. Yield 420 milligrams, 2.1%.

The resulting product which had a melting point of 232° C. was identified by infrared analysis and chemical analysis as accomplished in Example IV with substantially identical results.

EXAMPLE VI

Preparation of 8,10-Dimethoxyjuloidine

A 3 liter round bottom flask equipped with a magnetic stirbar, heating jacket, condenser and nitrogen sweep was charged with 3,5-dimethoxyaniline (91.5 grams, 0.60 mole), 1-bromo-3-chloropropane (450 milliliters) and diglyme (2 liters). The reaction mixture was heated at 130°-135° C. for 30 hours at which time high performance liquid chromatography showed that the reaction consisted mainly of 8,10-dimethoxyjuloidine (70 percent). The chloropropane and diglyme solvents was distilled from the product, first under aspirator vacuum and finally high vacuum, resulting in a syrup which was taken up in dichloromethane (1 liter). The dichloromethane solution was then extracted with saturated, aqueous, sodium bicarbonate solution (500 milliliters). The bicarbonate solution was then back extracted with 300 milliliters of dichloromethane, and the combined dichloromethane fractions were concentrated on the rotoevaporator. The resulting product mixture was then added dropwise to 2 liters of diethyl ether and the precipitate was filtered off after remaining at ambient temperature for 10 minutes. The diethyl ether solution was placed in the freezer overnight and more precipitate was filtered off. The ether was removed by evaporation, and the 8,10,-dimethoxyjuloidine intermediate product was purified by column chromatography on silica gel (eluent dichloromethane (25 percent)/hexanes (75 percent) and isolated as pale yellow crystals (31.4 grams, 23 percent).

EXAMPLE VII

Preparation of N,N-Dimethyl-3-(methylthio)benzenamine

A 250 milliliter round bottom flask topped with a Vigreux column, was charged with 3-amino-thioanisole (30.2 grams, 0.217 mole), trimethylphosphate (30.4 grams, 0.217 mole). This mixture was maintained under a nitrogen atmosphere. The reaction vessel was immersed in an oil bath and heated to 200° C. When the bath temperature reached 170° C., a vigorous reaction ensued. When the bath temperature reached 200° C., heating was continued with vigorous stirring to mix the two layers which formed during the course of the reaction. After 3 hours the heating bath was removed, and the reaction mixture was stirred while the reaction cooled to room temperature. When the stirring was stopped the reaction mixture separated into two layers; a pale yellow upper layer and a red lower layer. The reaction flask was then filled with 4N NaOH solution and heated at 70° C. with stirring (1.5 hours) under nitrogen. The reaction mixture was then diluted to 350 milliliters with 4N NaOH and stirred at 20° C. overnight. After further dilution to 1300 milliliters with water to prevent sodium phosphate from precipitating out during the extraction, the reaction mixture was extracted with diethyl ether (3×500 milliliters). The above intermediate product was isolated by evaporation of the ether as a brown syrup. Distillation under high vacuum (bp 95°, 0.2 Torr) gave a colorless liquid (20.6 grams, 57 percent).

EXAMPLE VIII

Preparation of 8,10-Dihydroxyjulolidine

A 500 milliliter round bottomed flask, equipped with a thermometer, magnetic stirbar, condenser, a nitrogen inlet tube and a pressure equalizing dropping funnel was charged with 8,10-dimethoxyjulolidine prepared in accordance with Example VI (25.8 grams, 0.111 mole) and dichloromethane (150 milliliters). Boron tribromide (250 milliliters of 1M dichloromethane solution) was added at a constant rate so that the reaction temperature did not rise above 30° C. (105 minutes). After the addition was complete the dark brown heterogeneous mixture was stirred overnight. The excess boron tribromide was destroyed by the cautious addition of water. When the liberation of hydrogen bromide was complete both the aqueous and the organic phases were evaporated to a dry powder and this powder was dried under high vacuum in a desiccator over potassium hydroxide at 50° C. overnight. The above product was isolated by chromatography on a short column of silica gel by elution with hexane-isopropanol (10 percent) to give yellow, oxygen sensitive crystals (10.0 grams, 44 percent) melting point 168 to 173 degrees centigrade.

EXAMPLE IX

The Synthesis of Bis-9(8,10-dihydroxyjulolidinyl)squaraine

A 300 milliliter 3-necked round bottomed flask equipped with a thermometer, magnetic stirbar and Dean Stark trap, topped by a condenser and nitrogen inlet tube, was charged with squaric acid (1.39 grams, 0.0122 mole), toluene (60 milliliters) and n-butanol (60 milliliters). The reaction mixture was heated in an oil bath until refluxing began 105° C. When solution of the squaric acid was complete (15 minutes) 8,10-dihydroxyjulolidine (5.0 grams, 0.0244 mole), prepared in accordance with Example VIII was added in one portion and the reaction mixture immediately turned green. Refluxing was continued and green crystals began to precipitate from the reaction mixture (10 minutes). After refluxing had been continued for one hour subsequent to the addition of 8,10-dihydroxyjulolidine, the reaction mixture was cooled to 25° C. and filtered to collect the above squaraine product as fine green crystals (5.76 grams, 98 percent).

In dichloromethane the squaraine product showed a strong visible absorption peak at 672 nanometers, with an extinction coefficient of 170,000.

EXAMPLE X

Three photoresponsive devices containing the squaraines indicated as the photoconductive material, and a charge transport layer of an amine dispersed in a resinous binder, were prepared. Specifically, three photoreceptor devices were prepared by providing ball grained aluminum substrates, of a thickness of 150 microns, followed by applying thereto with a multiple clearance film applicator, in a wet thickness of 0.5 mils, a layer of N-methyl-3-aminopropyltrimethoxysilane, available from PCR Research Chemicals, Florida, in ethanol, in a 1:20 volume ratio. This layer was then allowed to dry for 5 minutes at room temperature, followed by curing for 10 minutes at 110° C. in a forced air oven.

Photoconductive layers containing 30 percent by weight of bis(2,6-dihydroxy-4-dimethylaminophenyl)-squaraine, 30 percent by weight of bis(4-dimethylamino-2-methylthiophenyl)squaraine, or 30 percent by weight of bis-9-(8-hydroxyjulolidinyl)squaraine were then prepared as follows:

In separate 2 oz. amber bottles there was added 0.33 grams of the respective squaraines, 0.75 grams of Vitel PE-200 ®, a polyester available from Goodyear, 85 grams of ⅛" stainless steel shot, and 20 ml of methyl ethyl ketone/toluene solvent mixture, in a 4:1 volume ratio. The above mixtures were placed on a ball mill for 24 hours. The resulting slurries were then coated on the aluminum substrates with a multiple clearance film applicator, to a wet thickness of 1 mil. The layers were allowed to air dry for 5 minutes. The resulting three devices were dried at 135° C. for 6 minutes in a forced air oven. The dry thickness of each squaraine layer was 1 micron.

Each of the above photoconductive layers were then overcoated with a charge transport layer, which was prepared as follows:

A transport layer composed of 50 percent by weight Makrolon ®, a polycarbonate resin available from Larbensabricken Bayer A.G., was mixed with 50 percent by weight N,N'-bis(3-methylphenyl)-1,1'-biphenyl-4,4'-diamine. This solution was mixed to 9 percent by weight in methylene chloride. All of these components were placed in an amber bottle and dissolved. The mixture was coated to give a layer with a dry thickness of 30 microns on top of the above photoconductive layers, using a multiple clearance film applicator (15 mils wet gap thickness). The resulting devices were then air dried at room temperature for 20 minutes and then in a forced air oven at 135° C. for 6 minutes.

EXAMPLE XI

A photoreceptor device was prepared by repeating the procedure of Example X wherein the photoconductive layer contained the bis-9-(8-hydroxyjulolidinyl)-squaraine as prepared by the procedure of Example II. More specifically, there was prepared a photoreceptor device by providing a ball grained aluminum substrate, of a thickness of about 150 microns, and applying thereto with a multiple clearance film applicator, in a wet thickness of 0.5 mils, a layer of N-methyl-3-aminopropyltrimethoxysilane, in ethanol, in a 1:20 volume ratio, available PCR Research Chemicals, Florida, which layer was then allowed to dry for 5 minutes at room temperature, followed by curing for 10 minutes at 110° C. in a forced air oven.

A photoconductive layer containing 30 percent by weight of the bis-9-(8-hydroxyjulolidinyl)squaraine of Example II, was then prepared as follows:

In a 2 oz. amber bottle there was added 0.33 grams of the squaraine, 0.75 grams of Vitel PE-200 ®, a polyester available from Goodyear, 85 grams of ⅛" stainless steel shot, and 20 ml of methyl ethyl ketone/toluene solvent mixture, in a 4:1 volume ratio. The above mixture was placed on a ball mill for 24 hours. The resulting slurry was then coated on the above substrate with a multiple clearance film applicator, to a wet thickness of 1 mil. The layer was allowed to air dry for 5 minutes. This device was then dried at 25° C. for 17 hours in a vacuum oven. The dry thickness was 1 micron.

The above photoconductive layer was then overcoated with a charge transport layer, which was prepared as follows:

A transport layer containing 50 percent by weight Makrolon ®, a polycarbonate resin available from Larbensabricken Bayer A.G., was mixed with 50 percent by weight N,N'-diphenyl-N,N'-bis(3-methylphenyl)-1,1'-biphenyl-4,4'-diamine. This solution was mixed to 9 percent by weight in methylene chloride. All of these components were placed in an amber bottle and dissolved. The mixture was coated to give a layer with a dry thickness of 15 microns on top of the squaraine photoconductive layer, using a multiple clearance film applicator, 8 mils wet gap thickness. The device was air dried at room temperature for 20 minutes and then in a vacuum oven at 25° C. for 17 hours.

There resulted a photoresponsive device containing an aluminum substrate, a photoconductive layer of bis-9-(8-hydroxyjulolidinyl)squaraine, 1 micron in thickness, and a charge transport layer of the diamine, 50 percent by weight dispersed in 50 percent by weight of the polycarbonate resinous binder.

EXAMPLE XII

There was prepared a photoresponsive device by essentially repeating the procedure of Example X with the exception that the squaraine photoconductive layer was overcoated on the charge transport layer, thus resulting in a device containing an aluminum substrate overcoated with the diamine charge transport layer, which in turn was overcoated with the squaraine photoconductive layer containing the squaraine as prepared in accordance with Example I. More specifically, a photoresponsive device was prepared by providing a ball grained aluminum substrate, of a thickness of about 150 microns, and applying thereto with a multiple clearance film applicator, in a wet thickness of 0.5 mils, a layer of N-methyl-3-aminopropyltrimethoxysilane, available from PCR Research Chemicals, Florida. This layer was then allowed to dry for 5 minutes at room temperature, followed by curing for 10 minutes at 110° C. in a forced air oven.

The silane layer was overcoated with a charge transport layer which was prepared as follows:

A transport layer containing 50 percent by weight Makrolon ®, a polycarbonate resin available from Larbensabricken Bayer A.G., was mixed with 50 percent by weight N,N'-diphenyl-N,N'-bis(3-methylphenyl)-1,1'-biphenyl-4,4'-diamine. This solution was mixed to 9 percent by weight in methylene chloride. All of these components were placed in an amber bottle and dissolved. The mixture was coated to give a layer with a dry thickness of 15 microns on top of the silane layer, using a multiple clearance film applicator (8 mils wet gap thickness). The device was air dried at room temperature for 20 minutes, and then annealed at 135° C. in a forced air oven for 6 minutes.

A photoconductive layer containing 30 percent by weight of the bis-9-(8-hydroxyjulolidinyl)squaraine of Example I, was then prepared as follows:

In a 2 oz. amber bottle were added 0.33 grams of the squaraine, 0.75 grams of Vitel PE-200 ®, a polyester available from Goodyear, 85 grams of $\frac{1}{8}$" stainless steel shot, and 20 ml of methyl ethyl ketone/toluene solvent mixture, in a 4:1 volume ratio. The above mixture was then placed on a ball mill for 24 hours. The resulting slurry was then coated on the diamine transport layer with a multiple clearance film applicator, to a wet thickness of 1 mil. This layer was allowed to air dry for 10 minutes and the resulting device was then dried at 135° C. for 6 minutes in a forced air oven, to a dry thickness of 1 micron for the squaraine layer.

EXAMPLE XIII

A photoreceptor device was prepared by repeating the procedure of Example VIII with the exception that the photoconductive layer contained the squaraine composition of Example IV. More specifically, there was prepared a photoresponsive device by providing a ball grained aluminum substrate, of a thickness of 150 microns, and applying thereto with a multiple clearance film applicator, in a wet thickness of 0.5 mils, a layer of N-methyl-3-aminopropyltrimethoxysilane, available from PCR Research Chemicals, Florida. This layer was allowed to dry for 5 minutes at room temperature, followed by curing for 10 minutes at 110° C. in a forced air oven.

A photoconductive layer containing 30 percent by weight of the bis(4-dimethylamino-2-methylthiophenyl)squaraine of Example IV was then prepared as follows:

In a 2 oz. amber bottle were added 0.33 grams of the squaraine, 0.75 grams of Vitel PE-200 ®, a polyester available from Goodyear, 85 grams of $\frac{1}{8}$" stainless steel shot, and 20 ml of methyl ethyl ketone/toluene solvent mixture in a 4:1 volume ratio. The above mixture was placed on a ball mill for 24 hours. The resulting slurry was then coated on the silane layer with a multiple clearance film applicator, to a wet thickness of 0.5 mil. This layer was allowed to air dry for 5 minutes, and the resulting device was then dried at 135° C. for 6 minutes in a forced air oven to a dry thickness for the squaraine layer of 0.5 microns.

The above photoconductor squaraine layer was then overcoated with a charge transport layer prepared as follows:

A transport layer containing 50 percent by weight Makrolon ®, a polycarbonate resin available from Larbensabricken Bayer A.G., was mixed with 50 percent by weight N,N'-diphenyl-N,N'-bis(3-methylphenyl)-1,1'-biphenyl-4,4'-diamine. This solution was mixed to 9 percent by weight in methylene chloride. All of these components were then placed in an amber bottle and dissolved. The mixture was coated to give a layer with a dry thickness of 30 microns, on top of the photoconductive layer, using a multiple clearance film applicator, 15 mils wet gap thickness. The device was air dried at room temperature for 20 minutes and then in a forced air oven at 135° C. for six minutes.

EXAMPLE XIV

There was prepared a number of photoresponsive devices containing a photogenerating layer and a photoconductive layer, which devices were sensitive to light in the visible and/or infrared region of the spectrum, thus enabling them to be useful in xerographic printing systems. Thus a photoreceptive device was prepared by providing an aluminized Mylar substrate in a thickness of 3 mils and applying thereto a layer of 0.5 percent by weight duPont 49,000 adhesive, a polyester available from duPont, in methylene chloride and 1,1,2-trichloroethane (4:1 volume ratio) with a Bird applicator, to a wet thickness of 0.5 mils. The layer was allowed to dry for one minute at room temperature, and 10 minutes at 100° C. in a forced air oven. The resulting layer had a dry thickness of about 0.05 microns.

A photogenerator layer containing 10 percent by volume trigonal selenium, and 25 percent by volume of N,N'-diphenyl-N,N'-bis(3-methylphenyl)1,1'-biphenyl-4,4'-diamine in 65 volume percent of polyvinyl carbazole was then prepared as follows:

To a 2 oz. amber bottle was added 0.8 grams polyvinyl carbazole and 14 milliliters, 1:1 volume ratio, tetrahydrofuran:toluene. There was then added to this solution 0.8 grams of trigonal selenium and 100 grams of stainless steel shot, $\frac{1}{8}$" in diameter. The above mixture was then placed on a ball mill for 72 to 96 hours. Subsequently, 5 grams of the resulting slurry were added to a solution of 0.18 grams of polyvinyl carbazole, and 0.15 grams of N,N'-diphenyl-N,N'-bis(3-methylphenyl)1,1'-biphenyl-4,4'-diamine, in 6.3 milliliters of tetrahydrofuran-toluene, volume ratio 1:1. This slurry was then placed on a shaker for 10 minutes. The resulting slurry was then coated on the above interface with a Bird applicator, wet thickness 0.5 mils. This layer was then dried at 135° C. for 6 minutes in a forced air oven, resulting in a dry thickness of 2.0 microns.

A photoconductive layer containing 30 percent by volume of the bis-9-(8-hydroxyjulolidinyl)squaraine of Example I was then prepared as follows:

In a 2 oz. amber bottle was added 0.76 grams of Formvar 12/85, commercially available from Monsanto and 16 milliliters tetrahydrofuran. Added to this solution was 0.36 grams of julolidinyl squaraine and 100 grams ⅛" stainless steel shot. The above mixture was placed on a ball mill for 24 hours. To 5 grams of this slurry was added 10 milliliters of additional solvent. This slurry was then coated on the above photogenerator layer with a Bird applicator, to a wet thickness of 0.5 mils. The resulting device was dried at 135° C. for 6 minutes in a forced air oven. The dry thickness of the photoconductive layer was 0.5 microns.

The above photoconductive layer was overcoated then with a charge transport layer which was prepared as follows:

A transport layer containing 50 percent by weight Makrolon ®, a polycarbonate resin having a molecular weight (Mw) of from about 50,000 to about 100,000 available from Larbensabricken Bayer A. G., was mixed with 50 percent by weight N,N'-diphenyl-N,N'-bis(3-methylphenyl)1,1'-biphenyl-4,4'-diamine. The resulting solution was mixed in 15 percent by weight of methylene chloride. All of these components were placed into an amber bottle and dissolved. The mixture was coated to a dry 25 micron thickness layer on top of the above photoconductive layer using a Bird applicator. During this coating process the humidity was equal to or less than 15 percent.

The resulting device containing all of the above layers was annealed at 135° C. in a forced air oven for 6 minutes.

EXAMPLE XV

A photoreceptive device was prepared by providing an aluminized Mylar substrate in a thickness of 3 mils, and applying thereto in a wet thickness of 0.5 mils, a layer of 0.5 percent by weight of duPont 49,000 adhesive, a polyester available from duPont, in methylene chloride and 1,1,2-trichloroethane (4:1 volume ratio) with a Bird applicator. This layer was then allowed to dry for one minute at room temperature and 10 minutes at 100° C. in a forced air oven. The resulting layer had a dry thickness of about 0.05 microns.

A photogenerator layer containing 30 percent by volume of trigonal selenium, 25 percent by volume of N,N'-diphenyl-N,N'-bis(3-methylphenyl)1,1'-biphenyl-4,4'-diamine and 45 volume percent of polyvinyl carbazole was prepared as follows:

In a 2 oz. amber bottle was added 0.8 grams polyvinyl carbazole and 18 milliliters, 1:1 volume ratio, tetrahydrofuran:toluene. There was then added to this solution 2.1 grams of trigonal selenium and 100 grams of stainless steel shot, ⅛" in diameter. The above mixture was then placed on a ball mill for 72 to 96 hours. In a 1 oz. amber bottle was added 0.04 grams N,N'-diphenyl-N,N'-bis(3-methylphenyl)1,1'-biphenyl-4,4'-diamine and 6.4 milliliters of tetrahydrofuran-toluene, volume ratio 1:1. Added to this solution was 2 grams of the ball milled slurry. This slurry was then placed on a shaker for 10 minutes. The resulting slurry was then coated on the above 49,000 adhesive layer with a Bird applicator, to a wet thickness 0.5 mils. This device was then allowed to air dry 1 to 5 minutes to a a dry thickness for the photogenerator layer of 0.5 microns. The resulting device was then dried at 135° C. for 6 minutes in a forced air oven.

A photoconductive layer containing 30 percent by volume of the bis-9-(8-hydroxyjulolidinyl)squaraine of Example II was prepared as follows:

In a 2 oz. amber bottle was added 0.76 grams Formvar ®12/85, and 16 milliliters tetrahydrofuran. Added to this solution was 0.36 grams of the bis-9-(8-hydroxyjulolidinyl) squaraine, and 100 grams ⅛" stainless steel shot. The above mixture was placed on a ball mill for 24 hours. To 5 grams of this slurry was added 10 milliliters of additional solvent. This slurry was then coated on the above generator layer with a Bird applicator, to a wet thickness of 0.5 mils. The resulting device was dried at 135° C. for 6 minutes in a forced air oven. The dry thickness of the photoconductive layer was 0.5 microns.

The above photoconductive layer was overcoated with a charge transport layer which was then prepared as follows:

A transport layer containg 50 percent by weight Makrolon ®, a polycarbonate resin having a molecular weight (Mw) of from about 50,000 to about 100,000 available from Larbensabricken Bayer A. G., was mixed with 50 percent by weight N,N'-diphenyl-N,N'-bis(3-methylphenyl)1,1'-biphenyl-4,4'-diamine. The resulting solution was mixed in 15 percent by weight of methylene chloride. All of these components were then placed into an amber bottle and dissolved. The mixture was coated to a dry 25 micron thickness layer on top of the above photoconductive layers using a Bird applicator. During this coating process the humidity was equal to or less than 15 percent.

The resulting device containing all of the above layers was annealed at 135° C. in a forced air oven for 6 minutes.

EXAMPLE XVI

A photoreceptive device was prepared by providing an aluminized Mylar substrate in a thickness of 3 mils, and applying thereto in a wet thickness of 0.5 mils, a layer of 0.5 percent by weight of duPont 49,000 adhesive, a polyester available from duPont, in methylene chloride and 1,1,2-trichloroethane (4:1 volume ratio) with a Bird applicator. The wet thickness was 0.5 mil. This layer was then allowed to dry for one minute at room temperature and 10 minutes at 100° C. in a forced air oven. The resulting layer had a dry thickness of about 0.05 microns.

A photogenerator layer containing 33 percent by volume of trigonal selenium, and 13 percent by volume of N,N'-diphenyl-N,N'-bis(3-methylphenyl)1,1'-biphenyl-4,4'-diamine in the phenoxy binder Bakelite available from Union Carbide was prepared as follows:

In a 4 oz. amber bottle was added 1.6 grams of the above phenoxy resin, 21 milliliters methyl ethyl ketone and 7 milliliters methoxy ethyl acetate. Added to this solution was 3.2 grams of trigonal selenium, and 200 grams ⅛" stainless steel shot. The above mixture was placed on a ball mill for 72-96 hours. This slurry was then coated on the above polyester with a Bird applicator, to a wet thickness of 0.5 mils. This layer was allowed to air dry 2-5 minutes. The dry thickness was 0.5 microns. This layer was then dried at 135° C. in forced air for 6 minutes.

A photoconductive layer containing 30 percent by volume of the bis(2,6-dihydroxy-4-dimethylaminophenyl)squaraine of Example III was then prepared as follows:

In a 2 oz. amber bottle was added 0.76 grams Monsanto Formvar 12/85, and 16 ml. of tetrahydrofuran. Added to this solution was 0.36 grams of bis(2,6-dihydroxy-4-dimethylaminophenyl)squaraine and 100 grams ⅛" stainless steel shot. The above mixture was placed on a ball mill for 24 hours. To 5 grams of this slurry was added 10 milliliters of additional solvent. This slurry was then coated on the above photogenerator with a Bird applicator, to a wet thickness of 0.5 mils. The resulting device was dried at 135° C. for 6 minutes in a forced air oven. The dry thickness of the photoconductive layer was 0.5 microns.

The above photoconductive layer was overcoated with a charge transport layer which was then prepared as follows:

A transport layer containing 50 percent by weight Makrolon ®, a polycarbonate resin having a molecular weight (Mw) of from about 50,000 to about 100,000 available from Larbensabricken Bayer A. G., was mixed with 50 percent by weight N,N'-diphenyl-N,N'-bis(3-methylphenyl)1,1'-biphenyl-4,4'-diamine. This solution was mixed in 15 percent by weight of methylene chloride. All of these components were placed into an amber bottle and dissolved. The mixture was coated to a dry 25 micron thickness layer on top of the generator layers using a Bird applicator. During this coating process the humidity was equal to or less than 15 percent.

The resulting device containing all of the above layers was annealed at 135° C. in a forced air oven for 6 minutes.

EXAMPLE XVII

A photoreceptive device was prepared by providing an aluminized Mylar substrate in a thickness of 3 mils, and applying thereto in a wet thickness of 0.5 mils, a layer of 0.5 percent by weight of duPont 49,000 polyester adhesive, in methylene chloride and 1,1,2-trichloroethane (4:1 volume ratio) with a Bird Applicator. The layer was allowed to dry for one minute at room temperature, and 10 minutes at 100° C. in a forced air oven. The resulting layer had a dry thickness of 0.05 microns.

There was then overcoated on the adhesive layer 49,000 by known vacuum evaporation processes, a layer of arsenic triselenide, 0.25 microns in thickness.

A photoconductive layer containing 30 percent by volume of the bis(4-dimethylamino-2-thiomethylphenyl)squaraine of Example IV was then prepared as follows:

In a 2 oz. amber bottle was added 0.76 grams Formvar 12/85, and 16 milliliters of tetrahydrofuran. Added to this solution was 0.36 grams of bis(4-dimethylamino-2-methylthiophenyl)squaraine, and 100 grams ⅛" stainless steel shot. The above mixture was placed on a ball mill for 24 hours. To 5 grams of this slurry was added 10 milliliters of additional tetrahydrofuran. The resulting slurry was then coated on the above photogenerator layer with a Bird applicator, to a wet thickness of 0.5 mils. The resulting layer was allowed to air dry for 5 minutes. This device was dried at 135° C. for 6 minutes in a forced air oven. The dry thickness of the photoconductive layer was 0.5 microns.

The above photoconductive layer was then overcoated with a charge transport layer which was prepared as follows:

A transport layer containing 50 percent by weight Makrolon ®, a polycarbonate resin having a molecular weight (Mw) of from about 50,000 to about 100,000 available from Larbensabricken Bayer A. G., was mixed with 50 percent by weight N,N'-diphenyl-N,N'-bis(3-methylphenyl)1,1'-biphenyl-4,4'-diamine. This solution was mixed in 15 percent by weight of methylene chloride. All of these components were placed into an amber bottle and dissolved. The mixture was coated to a dry 25 micron thickness on top of the above photoconductive layer using a Bird applicator. During this coating process the humidity was equal to or less than 15 percent.

The resulting device containing all of the above layers was annealed at 135° C. in a forced air oven for 6 minutes.

EXAMPLE XVIII

A photoreceptive device was prepared by providing an aluminized Mylar substrate in a thickness of 3 mils, and applying thereto in a wet thickness of 0.5 mils, a layer of 0.5 percent by weight of duPont 49,000 adhesive, a polyester available from duPont, in methylene chloride and 1,1,2-trichloroethane (4:1 volume ratio) with a Bird applicator. The wet thickness was 0.5 mil. This layer was then allowed to dry for one minute at room temperature and 10 minutes at 100° C. in a forced air oven. The resulting layer had a dry thickness of about 0.05 microns.

A photoconductive layer containing 30 percent by volume of the bis(4-dimethylamino-2-methylthiophenyl)squaraine of Example V was prepared as follows:

In a 2 oz. amber bottle is added 0.76 grams Formvar 12/85, (Monsanto) and 16 milliliters tetrahydrofuran. Added to this solution was 0.36 grams of the squaraine and 100 grams ⅛" stainless steel shot. The above mixture was placed on a ball mill for 24 hours. To 5 grams of this slurry was added 10 milliliters of additional solvent. This slurry was then coated on the above adhesive interface with a Bird applicator, to a wet thickness of 0.5 mils. The resulting device was dried at 135° C. for 6 minutes in a forced air oven. The dry thickness of the photoconductive layer was 0.5 microns.

A generator layer containing 10 percent by volume of trigonal selenium, and 25 percent by volume of N,N'-diphenyl-N,N'-bis(3-methylphenyl)1,1'-biphenyl-4,4'-diamine and 65 volume percent of polyvinyl carbazole was prepared as follows:

In a 2 oz. amber bottle was added 0.8 grams polyvinyl carbazole and 14 milliliters, 1:1 volume ratio, tetrahydrofuran:toluene. There was then added to this solution 0.8 grams of trigonal selenium and 100 grams of stainless steel shot, ⅛" in diameter. The above mixture was then placed on a ball mill for 72 to 96 hours. In a 1 oz. amber bottle was added 0.15 grams N,N'-diphenyl-N,N'-bis(3-methylphenyl)1,1'-biphenyl-4,4'-diamine, 0.18 grams polyvinylcarbazole, and 6.3 milliliters of tetrahydrofurantoluene, volume ratio 1:1. Added to this solution was 5 grams of the ball milled slurry. The slurry formed was then placed on a shaker for 10 minutes. The resulting slurry was then coated on the above photoconductive layer with a Bird applicator, to a wet thickness 0.5 mils. This layer was then dried at 135° C. for 6 minutes in a forced air oven, resulting in a dry thickness for the generator layer of 2.0 microns.

The above photogenerating layer was overcoated with a charge transport layer which was then prepared as follows:

A transport layer containing 50 percent by weight Makrolon ®, a polycarbonate resin having a molecular weight (Mw) of from about 50,000 to about 100,000 available from Larbensabricken Bayer A. G., was mixed with 50 percent by weight N,N'-diphenyl-N,N'-bis(3-methylphenyl)1,1'-biphenyl-4,4'-diamine. This solution was mixed in 15 percent by weight of methylene chloride. All of these components were placed into an amber bottle and dissolved. The mixture was coated to a dry 25 micron thickness layer on top of the photogenerator layer using a Bird applicator. During this coating process the humidity was equal to or less than 15 percent.

The resulting device containing all of the above layers was annealed at 135° C. in a forced air oven for 6 minutes.

EXAMPLE XIX

A photoreceptive device was prepared by providing an aluminized Mylar substrate in a thickness of 3 mils, and applying thereto in a wet thickness of 0.5 mils, a layer of 0.5 percent by weight of duPont 49,000 adhesive, a polyester available from duPont, in methylene chloride and 1,1,2-trichloroethane (4:1 volume ratio) with a Bird applicator. This layer was then allowed to dry for one minute at room temperature and 10 minutes at 100° C. in a forced air oven. The resulting layer had a dry thickness of about 0.05 microns.

A photoconductive layer containing 30 percent by volume of the bis-9-(8-hydroxyjulolidinyl)squaraine of Example I was prepared as follows:

In a 2 oz. amber bottle was added 0.76 grams Monsanto Formvar12/85 and 16 ml tetrahydrofuran. Added to this solution was 0.36 grams of the bis-9-(8-hydroxyjulolidinyl)squaraine and 100 grams ⅛" stainless steel shot. The above mixture was placed on a ball mill for 24 hours. To 5 grams of this slurry was added 10 milliliters of additional solvent. The slurry formed was then coated on the above adhesive layer with a Bird applicator, to a wet thickness of 0.5 mils. The resulting device was dried at 135° C. for 6 minutes in a forced air oven. The dry thickness of the photoconductive layer was 0.5 microns.

A photogenerating layer containing 33 percent by volume of trigonal selenium, and 13 percent by volume of N,N'-diphenyl-N,N'-bis(3-methylphenyl)1,1'-biphenyl-4,4'-diamine in a Bakelite phenoxy binder was then prepared as follows:

In a 4 oz. amber bottle was added 1.6 grams of the above phenoxy resin, 21 milliliters methyl ethyl ketone and 7 milliliters methoxy ethyl acetate. Added to this solution was 3.2 grams trigonal selenium, and 200 grams ⅛" stainless steel shot. The above mixture was placed on a ball mill for 72–96 hours. The resulting slurry was then coated on the above photoconductive layer with a Bird applicator, to a wet thickness of 0.5 mils. The resulting device was allowed to air dry 2–5 minutes, followed by drying at 135° C. in forced air oven for 6 minutes. The dry thickness of the photogenerating layer was 0.5 microns.

The above photogenerating layer was overcoated with a charge transport layer which was then prepared as follows:

A transport layer containing 50 percent by weight Makrolon ®, a polycarbonate resin having a molecular weight (Mw) of from about 50,000 to about 100,000 available from Larbensabricken Bayer A. G., was mixed with 50 percent by weight N,N'-diphenyl-N,N'-bis(3-methylphenyl)1,1'-biphenyl-4,4'-diamine. This solution was mixed in 15 percent by weight of methylene chloride. All of these components were placed into an amber bottle and dissolved. The mixture was coated to a dry 25 micron thickness layer on top of the above photogenerator layer using a Bird applicator. During this coating process the humidity was equal to or less than 15 percent.

The resulting device containing all of the above layers was annealed at 135° C. in a forced air oven for 6 minutes.

Numerous other photoresponsive devices were prepared by repeating the procedures of the above examples with the exception that there was selected as the photogenerating composition a selenium tellurium alloy, containing 75 percent by weight of selenium, and 25 percent by weight of tellurium, or an arsenic selenium alloy, containing 99.9 percent by weight of selenium, and 0.1 percent by weight of arsenic.

Each of the photoresponsive devices of Examples X–XIX were then tested for photosensitivity in the visible and infra-red region of the spectrum by negatively charging with a corotron to a −800 volts the devices of Examples X, XI, and XIV to XIX, while the device of Examples XII was positively charged with a corotron to 800 volts, followed by simultaneously exposing each device to monochromatic light in a wavelength range of from about 400 to about 1,000 nanometers. The surface potential of each device was then measured with an electrical probe after exposure to given wavelengths. The percent discharge of each device was then calculated as disclosed hereinbefore, which percent discharge indicates photoresponse.

Figure 9:
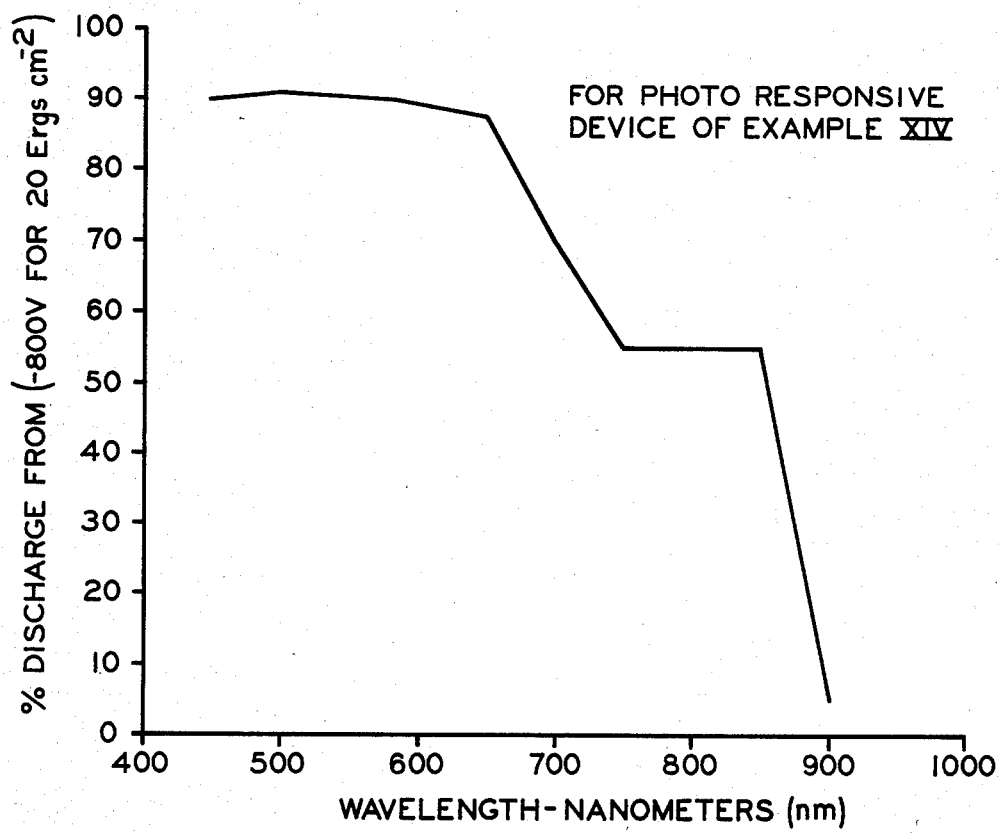
FIG. 9 represents the percent discharge for a photoresponsive device containing the squaraine composition of the present invention, reference Example XIV, for 20 ergs cm$^{-2}$ exposure of this device from a dark development potential ($V_{DDP}$) of $-800$ volts as a function of light exposed in the wavelength of 400 to 1,000 nanometers. This figure demonstrates the visible and infra-red sensitivity of the device involved.

The devices of Examples XIV–XIX, had sufficient discharge so as to respond to light in a wavelength range of from about 400 to about 950 nanometers, reference FIG. 9 for Example XIV, indicating both visible and infra-red photosensitivity for these devices. Generally trigonal selenium alone has no photoresponse in the infra-red region of the spectrum, but is responsive in the visible, while the squaraines of the present invention have photosensitivity in the infrared region of the spectrum, and are inferior in their response to trigonal selenium in the visible region of the spectrum.

Also the photoresponsive devices as prepared in Examples X to XIII, were tested for photosensitivity by charging each of the devices in the dark to a surface potential of 1,000 volts, followed by measuring with an electrical probe the amount of light energy of monochromatic light supplied by a Xenon lamp, in ergs per centimeter squared required to discharge each device to one half of its surface potential. A low discharge number, for example below 100, indicates excellant photosensitivity for the device involved.

At wavelengths of 400 to 700 nanometers the devices of Example X, containing bis(2,6-dihydroxy-4-dimethylaminophenyl)squaraine XI, XII, and XIII had photodischarge numbers of 70, 25, 45, and 80 respectively, while at wavelengths of 830 nanometers the devices of Examples XI, XII, and XIII had photodischarge numbers of 14, 15, and 33 respectively.

Although the invention has been described with reference to specific preferred embodiments, it is not intended to be limited thereto, rather those skilled in the art will recognize variations and modifications may be made therein which are within the spirit of the present invention and within the scope of the following claims.

We claim:

1. A squaraine of the formula

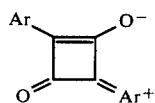

wherein Ar is selected from the moieties specified resulting in the following squaraines:

I. bis-9-(8-hydroxyjulolidinyl)squaraine

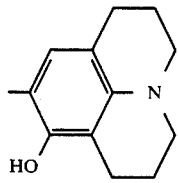

II. bis-9-(8,10-dihydroxyjulolidinyl)squaraine

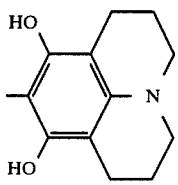

III. bis(4-dimethylamino-2-methylthiophenyl)squaraine

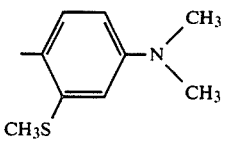

and

IV. bis(2,6-dihydroxy-4-dimethylaminophenyl)squaraine

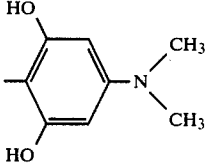

2. The squaraine bis-9-(8-hydroxyjulolidinyl)squaraine.

3. The squaraine bis-9-(8,10 dihydroxyjulolidinyl)squaraine.

4. The squaraine bis(4-dimethylamino-2-methylthiophenyl)squaraine.

5. The squaraine bis(2,6-dihydroxy-4-dimethylaminophenyl)squaraine.

* * * * *